US006295865B1

(12) United States Patent
Cherry

(10) Patent No.: US 6,295,865 B1
(45) Date of Patent: Oct. 2, 2001

(54) MOISTURE LEVEL INDICATOR

(76) Inventor: Stephen Cherry, 9 Braybank, Old Mill Lane, Bray Maidenhead Berkshire, SL6 2BQ (GB)

(*) Notice: Subject to any disclaimer, the term of this patent is extended or adjusted under 35 U.S.C. 154(b) by 0 days.

(21) Appl. No.: 09/199,104

(22) Filed: Nov. 25, 1998

(51) Int. Cl.⁷ .................................................. G01N 5/02
(52) U.S. Cl. .................................................. 73/73; 73/76
(58) Field of Search ........................... 73/73, 862.541, 73/76; 177/50, 239, 240

(56) References Cited

U.S. PATENT DOCUMENTS 4,316,384 * 2/1982 Pommer et al. ........................ 73/76
4,753,889 * 6/1988 Collins ..................................... 73/76
4,798,252 * 1/1989 Knothe et al. ........................... 73/76
4,838,705 * 6/1989 Byers, Jr.et al. ........................ 73/76

* cited by examiner

Primary Examiner—Hezron Williams
Assistant Examiner—Katina Wilson

(57) ABSTRACT

A moisture level indicator system is provided including a base and at least one weight sensor positioned on the base for determining a current weight supported thereon. Also included is a reset push switch mounted on the base and adapted to generate a reset signal. Next provided is a processor positioned within the base for recording a predetermined set weight on the base that is received via the weight sensor upon the receipt of the reset signal. The processor is further adapted to provide an indication of a difference between the predetermined set weight and a current weight supported on the base.

7 Claims, 2 Drawing Sheets

MOISTURE LEVEL INDICATOR

BACKGROUND OF THE INVENTION

1. Field of the Invention

The present invention relates to moisture sensors and more particularly pertains to a new moisture level indicator for monitoring a moisture level within a plant.

2. Description of the Prior Art

The use of moisture sensors is known in the prior art. More specifically, moisture sensors heretofore devised and utilized are known to consist basically of familiar, expected and obvious structural configurations, notwithstanding the myriad of designs encompassed by the crowded prior art which have been developed for the fulfillment of countless objectives and requirements.

Known prior art includes U.S. Pat. No. 4,454,831; U.S. Pat. No. 4,165,633; U.S. Pat. No. 5,020,261; U.S. Pat. No. 4,909,340; U.S. Pat. No. 3,293,799; U.S. Pat. No. 5,361,534; U.K. Patent No. GB 2307560 A; U.K. Patent No. GB 2268594 A; U.K. Patent No. GB 2268593 A; U.K. Patent No. GB 2247321 A; and U.K. Patent No. GB 2229541 A.

In these respects, the moisture level indicator according to the present invention substantially departs from the conventional concepts and designs of the prior art, and in so doing provides an apparatus primarily developed for the purpose of monitoring a moisture level within a plant.

SUMMARY OF THE INVENTION

In view of the foregoing disadvantages inherent in the known types of moisture sensors now present in the prior art, the present invention provides a new moisture level indicator construction wherein the same can be utilized for monitoring a moisture level within a plant.

The general purpose of the present invention, which will be described subsequently in greater detail, is to provide a new moisture level indicator apparatus and method which has many of the advantages of the moisture sensors mentioned heretofore and many novel features that result in a new moisture level indicator which is not anticipated, rendered obvious, suggested, or even implied by any of the prior art moisture sensors, either alone or in any combination thereof.

To attain this, the present invention generally comprises a base having a bottom face with a substantially planar circular configuration. A peripheral side wall of the base is equipped with a substantially frusto-conical configuration. A recess is formed in a top face of the base, as shown in FIG. 3. The base further includes a substantially disk-shaped plate with a height less than that of the recess. The plate is preferably freely positioned within the recess. As further shown in FIG. 3, the bottom face of the base is lined with an elastomeric pad. Inset within the top face of the base is at least one weight sensor with a transducer extending upwardly therefrom. Such transducer is adapted for supporting the plate of the base for determining a current weight supported thereon. Also mounted on the base is a temperature sensor for determining a current temperature. A display is positioned on the peripheral side wall of the base for displaying a plurality of numerals upon the receipt thereof. As shown in FIG. 4, a timer is positioned within the base for tracking a predetermined amount of time. Mounted on the peripheral side wall of the base is a reset push button which is spaced with respect to the display by about 90 degrees. In use, the reset button serves to generate a reset signal upon the depression thereof. Associated therewith is a status push button mounted on the peripheral side wall of the base adjacent to the display for generating a status signal upon the depression thereof. FIG. 4 shows a processor positioned within the base and connected between the weight sensor, temperature sensor, display, timer, and buttons. For powering purposes, the processor is preferably connected to a rechargeable battery and a solar cell which are positioned on the base. In use, the processor serves to record a predetermined set weight on the plate that is received via the weight sensor upon the receipt of the reset signal. The processor further is adapted to display a percent difference between a current weight on the plate and the predetermined set weight and further a current temperature for the predetermined amount of time. It should be noted that such difference and temperature are only depicted upon the receipt of the status signal.

There has thus been outlined, rather broadly, the more important features of the invention in order that the detailed description thereof that follows may be better understood, and in order that the present contribution to the art may be better appreciated. There are additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in anyway.

It is therefore an object of the present invention to provide a new moisture level indicator apparatus and method which has many of the advantages of the moisture sensors mentioned heretofore and many novel features that result in a new moisture level indicator which is not anticipated, rendered obvious, suggested, or even implied by any of the prior art moisture sensors, either alone or in any combination thereof.

It is another object of the present invention to provide a new moisture level indicator which may be easily and efficiently manufactured and marketed.

It is a further object of the present invention to provide a new moisture level indicator which is of a durable and reliable construction.

An even further object of the present invention is to provide a new moisture level indicator which is susceptible of a low cost of manufacture with regard to both materials and labor, and which accordingly is then susceptible of low prices of sale to the consuming public, thereby making such moisture level indicator economically available to the buying public.

Still yet another object of the present invention is to provide a new moisture level indicator which provides in the apparatuses and methods of the prior art some of the advantages thereof, while simultaneously overcoming some of the disadvantages normally associated therewith.

Still another object of the present invention is to provide a new moisture level indicator for monitoring a moisture level within a plant or the like.

Even still another object of the present invention is to provide a new moisture level indicator that includes a base and at least one weight sensor positioned on the base for determining a current weight supported thereon. Also included is a reset push switch mounted on the base and adapted to generate a reset signal. Next provided is a processor positioned within the base for recording a predetermined set weight on the base that is received via the weight sensor upon the receipt of the reset signal. The processor is further adapted to provide an indication of a difference between the predetermined set weight and a current weight supported on the base.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be made to the accompanying drawings and descriptive matter in which there are illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein.

DESCRIPTION OF THE PREFERRED EMBODIMENT

Figure 1:
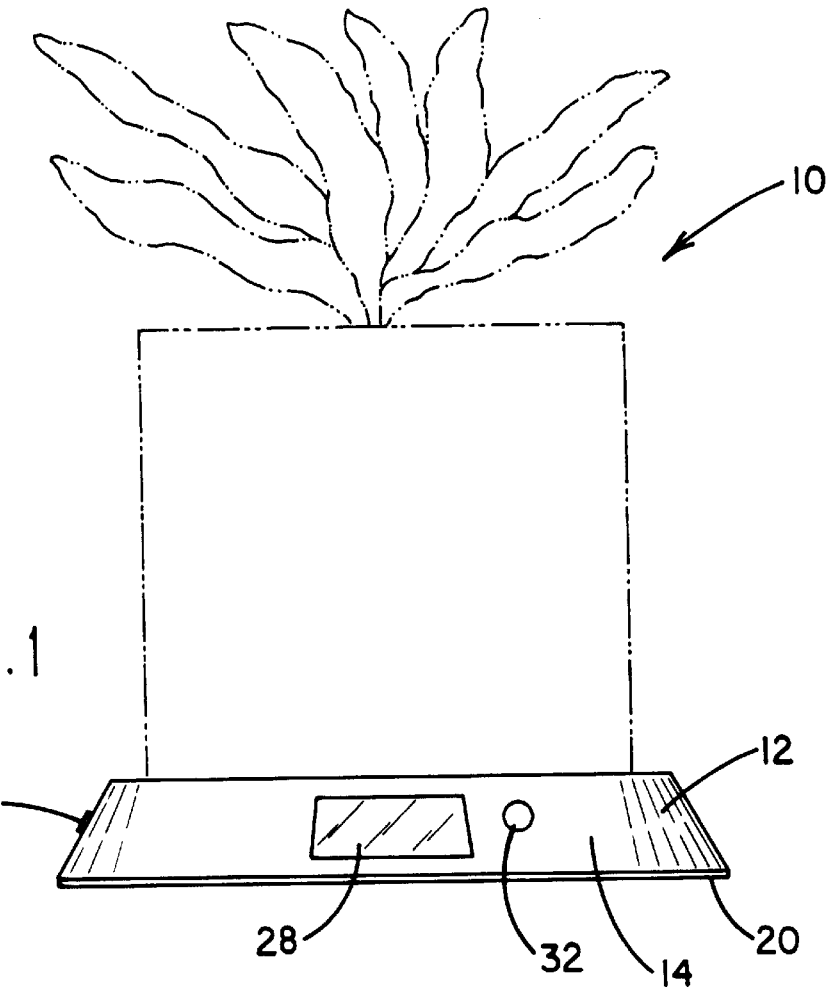
FIG. 1 is a side view of a new moisture level indicator according to the present invention.
Figure 2:
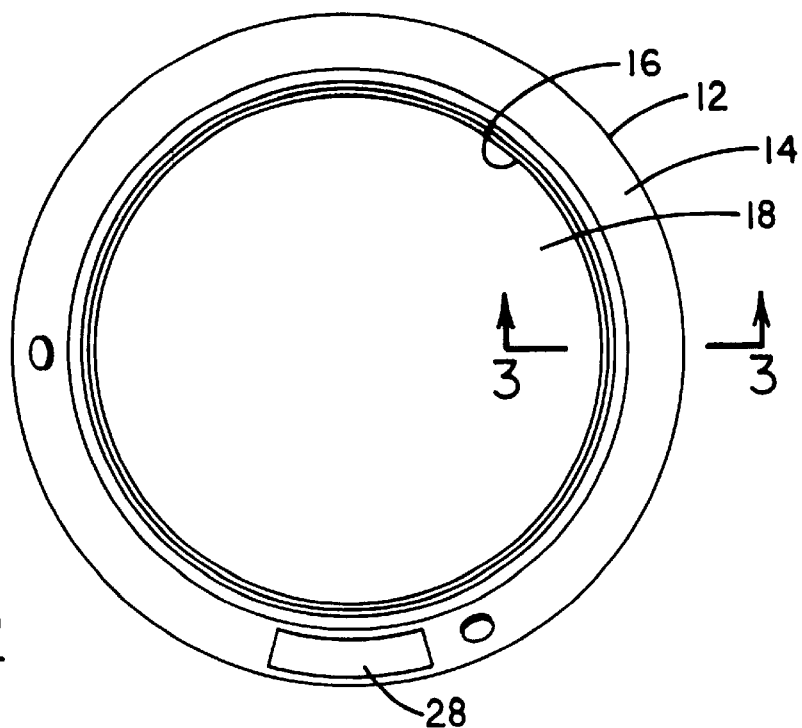
FIG. 2 is a top view of the present invention.

With reference now to the drawings, and in particular to FIGS. 1 through 4 thereof, a new moisture level indicator embodying the principles and concepts of the present invention and generally designated by the reference numeral 10 will be described.

Figure 3:
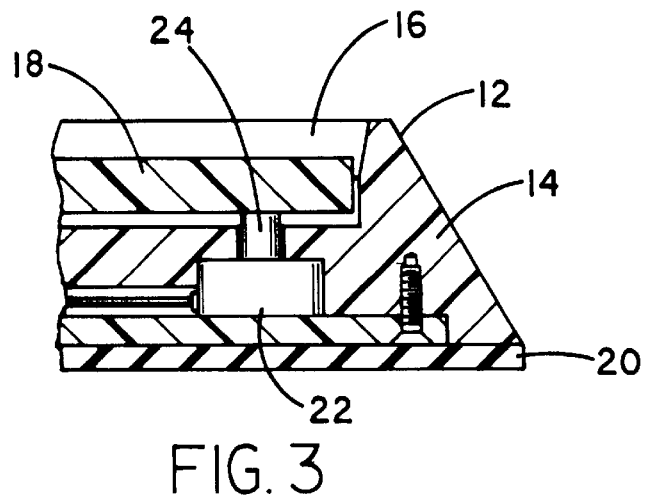
FIG. 3 is a side cross-sectional view of the present invention taken along line 3—3 shown in FIG. 2.

The present invention, designated as numeral 10, includes a base 12 having a bottom face with a substantially planar circular configuration. A peripheral side wall 14 of the base is equipped with a substantially frusto-conical configuration. A recess 16 is formed in a top face of the base, as shown in FIG. 3. The base further includes a substantially disk-shaped plate 18 with a height less than that of the recess. The plate is preferably freely positioned within the recess. As further shown in FIG. 3, the bottom face of the base is lined with an elastomeric pad 20. In use, a plant or the like is positioned on the plate and within the recess.

Figure 4:
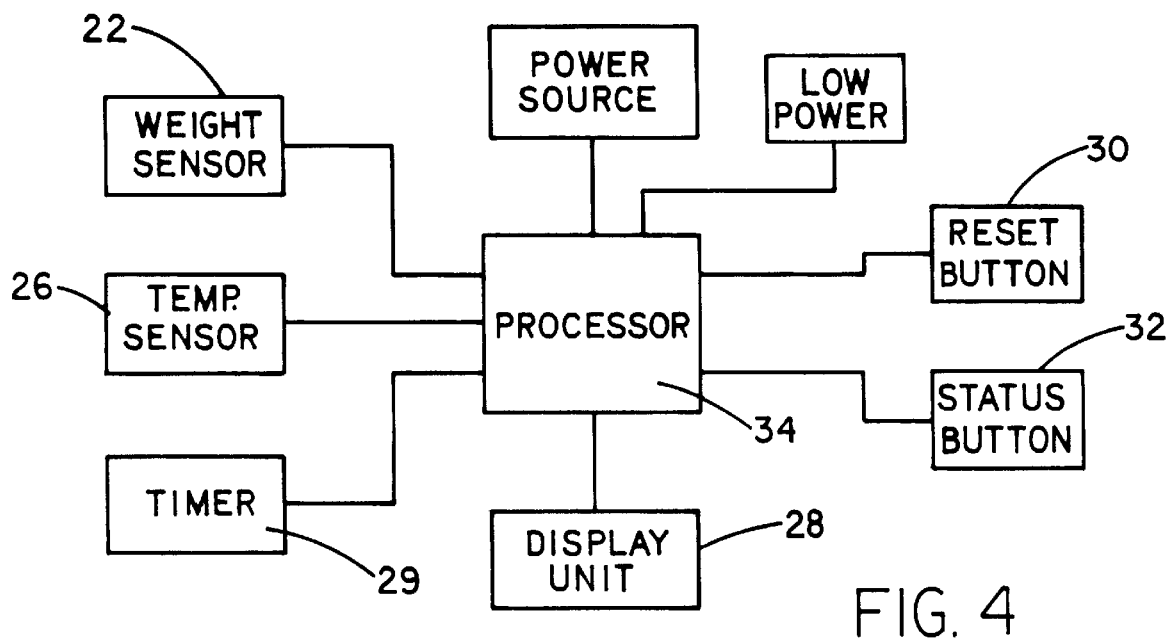
FIG. 4 is a schematic diagram of the present invention.

Inset within the top face of the base is at least one weight sensor 22 with a transducer 24 extending upwardly therefrom. Such transducer is adapted for supporting the plate of the base for determining a current weight supported thereon. Also mounted on the base is a temperature sensor 26 for determining a current ambient temperature. An LCD or LED display 28 is positioned on the peripheral side wall of the base for displaying a plurality of numerals upon the receipt thereof. As shown in FIG. 4, a timer 29 is positioned within the base for tracking a predetermined amount of time.

Mounted on the peripheral side wall of the base is a reset push button 30 which is spaced with respect to the display by about 90 degrees. In use, the reset button serves to generate a reset signal upon the depression thereof. Associated therewith is a status push button 32 mounted on the peripheral side wall of the base adjacent to the display for generating a status signal upon the depression thereof.

FIG. 4 shows a processor 34 positioned within the base and connected between the weight sensor, temperature sensor, display, timer, and buttons. For powering purposes, the processor is preferably connected to a rechargeable battery and a solar cell which are positioned on the base.

In use, the processor serves to record a predetermined set weight on the plate that is received via the weight sensor upon the receipt of the reset signal. The processor further is adapted to display a percent difference between a current weight on the plate and the predetermined set weight and further a current temperature for the predetermined amount of time. It should be noted that such difference and temperature are only depicted upon the receipt of the status signal. It may be assumed that such percent difference in weight is attributed to water loss which should be replenished.

As an option, a plurality of additional buttons are positioned on the base and connected to the processor each for carrying out an associated task. For example, included may be a button for displaying the current weight supported by the plate upon the depression thereof, a button for displaying the aforementioned weight difference in grams or other units upon the depression thereof, a button for displaying a duration since the reset button was last depressed upon the depression thereof, a button for displaying a duration since the status button was last depressed upon the depression thereof, a button for displaying the actual date and time upon the depression thereof, a button for recording a current date and time upon the depression thereof after the plant has been watered, and a button for displaying the previous dates and times the plant has been watered. Optionally, the temperature may be displayed via a dedicated push button. It should be noted that each of the foregoing quantities are depicted on the display for the predetermined amount of time when the associated button is depressed similar to that set forth hereinabove in relation to the percent difference.

Yet another option includes the incorporation of an audible alarm or a warning light which is positioned on the base and connected to the processor for actuating automatically upon the percent difference being at least a predetermined amount. Such predetermined amount may be selected by the user prior to use.

As to a further discussion of the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

I claim:

1. A moisture level indicator system for use with a plant comprising, in combination:
   a base including a bottom face with a substantially planar circular configuration, a peripheral side wall with a substantially frusto-conical configuration, and a recess formed in a top face thereof, the base further including a substantially disk-shaped plate with a height less than that of the recess and being freely positioned within the recess, wherein the bottom face of the base is lined with an elastomeric pad;
   at least one weight sensor inset within the top face of the base with a transducer extending upwardly therefrom for supporting the plate of the base for determining a current weight supported thereon;
   a temperature sensor mounted on the base for determining a current temperature of soil and plant in said base;
   a display positioned on the peripheral side wall of the base for displaying a plurality of numerals upon the receipt thereof;
   a timer positioned within the base for tracking a predetermined amount of time;
   a reset push button mounted on the peripheral side wall of the base and spaced with respect to the display by about 90 degrees, the reset button adapted to generate a reset signal upon the depression thereof;
   a status push button mounted on the peripheral side wall of the base adjacent to the display for generating a status signal upon the depression thereof; and
   a processor positioned within the base and connected between the weight sensor, temperature sensor, display, timer, buttons, and a solar cell for powering purposes, the processor adapted to record a predetermined set weight on the plate that is received via the weight sensor upon the receipt of the reset signal, the processor further adapted to display for the predetermined amount of time a percent difference between a current weight on the plate and the predetermined set weight and further a current temperature upon the receipt of the status signal.

2. A moisture level indicator system for use with a plant comprising, in combination:
   a base including a bottom face, a peripheral side wall, and a recess formed in a top face thereof, the base further including a substantially plate with a height less than that of the recess and being freely positioned within the recess, wherein the bottom face of the base is lined with an elastomeric pad;
   at least one weight sensor inset within the top face of the base with a transducer extending upwardly therefrom for supporting the plate of the base for determining a current weight supported thereon;
   a temperature sensor mounted on the base for determining a current temperature;
   a display positioned on the peripheral side wall of the base for displaying a plurality of numerals upon the receipt thereof;
   a timer positioned within the base for tracking a predetermined amount of time;
   a reset push button mounted on the peripheral side wall of the base, the reset button adapted to generate a reset signal upon the depression thereof;
   a status push button mounted on the peripheral side wall of the base adjacent to the display for generating a status signal upon the depression thereof; and
   a processor positioned within the base and connected between the weight sensor, temperature sensor, display, timer, buttons, and a solar cell for powering purposes, the processor adapted to record a predetermined set weight on the plate that is received via the weight sensor upon the receipt of the reset signal, the processor further adapted to display for the predetermined amount of time a percent difference between a current weight on the plate and the predetermined set weight and further a current temperature upon the receipt of the status signal.

3. A moisture level indicator system for determining the amount of moisture in soil containing a plant comprising in combination:
   a base having a bottom face and a peripheral side wall, said base having a recess formed in a top face thereof;
   at least one weight sensor positioned on the base for determining a current weight supported thereon;
   a reset push button mounted on the base and adapted to generate a reset signal; and
   a processor positioned within the base for recording a predetermined set weight on the base that is received via the weight sensor upon the receipt of the reset signal, the processor further adapted to provide an indication of a difference between the predetermined set weight and a current weight supported on the base;
   a display for depicting the difference; and
   wherein said processor is connected a solar cell for powering purposes.

4. A moisture level indicator system as set forth in claim 3 wherein the difference is a percent difference.

5. A moisture level indicator system as set forth in claim 3 wherein the difference is depicted for a predetermined amount of time.

6. A moisture level indicator system as set forth in claim 3 wherein the difference is depicted only upon the receipt of a status signal via a status button.

7. A moisture level indicator system as set forth in claim 3 and further including a temperature sensor, wherein the processor is adapted for indicating a current temperature of soil and plant contained in said base.

* * * * *